US010245578B2

(12) United States Patent
Klasovsky et al.

(10) Patent No.: US 10,245,578 B2
(45) Date of Patent: Apr. 2, 2019

(54) CHROMIUM- AND NICKEL-FREE HYDROGENATION OF HYDROFORMYLATION MIXTURES

(71) Applicant: Evonik Degussa GmbH, Essen (DE)

(72) Inventors: Florian Klasovsky, Haltern am See (DE); Robert Franke, Marl (DE); Frank Geilen, Haltern am See (DE); Andreas Jess, Bayreuth (DE); Wolfgang Korth, Bayreuth (DE); Thomas Quandt, Marl (DE); Arne Reinsdorf, Darmstadt (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/790,800

(22) Filed: Oct. 23, 2017

(65) Prior Publication Data

US 2018/0126361 A1     May 10, 2018

(30) Foreign Application Priority Data

Nov. 9, 2016 (EP) .................................... 16197935

(51) Int. Cl.
| | | |
|---|---|---|
| *C07C 29/00* | (2006.01) | |
| *B01J 23/00* | (2006.01) | |
| *B01J 21/00* | (2006.01) | |
| *B01J 23/72* | (2006.01) | |
| *B01J 21/08* | (2006.01) | |
| *B01J 37/02* | (2006.01) | |
| *B01J 37/08* | (2006.01) | |
| *C07C 29/141* | (2006.01) | |

(52) U.S. Cl.
CPC .............. *B01J 23/72* (2013.01); *B01J 21/08* (2013.01); *B01J 37/0203* (2013.01); *B01J 37/0236* (2013.01); *B01J 37/08* (2013.01); *C07C 29/141* (2013.01)

(58) Field of Classification Search
CPC .......... C07C 29/141; B01J 23/72; B01J 21/08
See application file for complete search history.

(56) References Cited

U.S. PATENT DOCUMENTS

| 3,677,969 | A | 7/1972 | Mertzweiller et al. |
|---|---|---|---|
| 4,677,234 | A | 6/1987 | Bartley |
| 5,591,873 | A | 1/1997 | Bankmann et al. |
| 6,201,160 | B1 | 3/2001 | Brudermuller et al. |
| 6,239,318 | B1 | 5/2001 | Schuler et al. |
| 6,680,414 | B2 | 1/2004 | Knoop et al. |
| 8,455,701 | B2 | 6/2013 | Kaizik et al. |
| 9,309,180 | B2 | 4/2016 | Kuppinger et al. |
| 9,567,276 | B2 | 2/2017 | Klasovsky et al. |
| 9,676,805 | B2 | 6/2017 | Dyballa et al. |
| 2011/0060169 | A1 | 3/2011 | Kaizik et al. |
| 2016/0176792 | A1 | 6/2016 | Klasovsky et al. |
| 2016/0236150 | A1 | 8/2016 | Geilen et al. |
| 2016/0257634 | A1 | 9/2016 | Dyballa et al. |

FOREIGN PATENT DOCUMENTS

| DE | 19842370 A1 | 3/2000 |
|---|---|---|
| EP | 2488478 B1 | 11/2015 |
| EP | 3037400 A1 | 6/2016 |
| WO | 9532171 A1 | 11/1995 |

OTHER PUBLICATIONS

Franke et al., U.S. Appl. No. 15/491,173, filed Apr. 19, 2017.

*Primary Examiner* — Sikarl A Witherspoon
(74) *Attorney, Agent, or Firm* — Philip P. McCann; Nexsen Pruet, PLLC

(57) ABSTRACT

The invention is concerned with catalysts for heterogeneous hydrogenation of oxo process aldehydes. The problem addressed by the invention is that of developing a catalyst containing neither chromium nor nickel. In addition, it is to enable the economically viable hydrogenation of aldehyde mixtures originating from industrial oxo processes on the industrial scale. For this purpose, the catalyst should not be reliant on costly precious metals such as Ru, Pd or Pt. This problem was solved by omitting the chromium and nickel in the preparation of a conventional Cu/Ni/Cr system, such that a catalyst wherein only copper occurs as hydrogenation-active component on the support material thereof, and not chromium or nickel, is obtained. What is surprising here is that a functioning catalyst for the purpose intended still arises at all even though two of three hydrogenation-active metals are omitted. However, this requires as necessary conditions that support material used is silicon dioxide and that the content of Cu and $SiO_2$ in the active catalyst is set accurately within very tight limits.

20 Claims, 4 Drawing Sheets

CHROMIUM- AND NICKEL-FREE HYDROGENATION OF HYDROFORMYLATION MIXTURES

This application claims the benefit of European Application No. 16197935.6 filed on Nov. 9, 2016, the disclosure of which is expressly incorporated herein by reference.

BACKGROUND

The invention relates to a process for preparing alcohols by hydrogenation of aldehydes, in which a feed mixture comprising at least one aldehyde and at least one accompanying component is contacted with a heterogeneous catalyst in the presence of hydrogen, giving a product mixture comprising at least the alcohol corresponding to the hydrogenated aldehyde and at least one by-product, wherein the catalyst comprises a support material and copper applied thereto.

The invention further relates to the preparation of the corresponding catalyst and the corresponding precursor, optional activation of the precursor and use of the active catalyst in the process.

Elimination of hydrogen (dehydrogenation) from an alcohol gives rise to an aldehyde. Conversely, alcohols can be prepared from aldehydes by hydrogenation (addition of hydrogen).

Hydrogenation in general is a reaction conducted very frequently in industry. Another specific reaction practised on the industrial scale is the hydrogenation of aldehydes, namely in the preparation of what are called oxo process alcohols.

Oxo process alcohols are alcohols which are prepared by way of hydroformylation (oxo reaction). In hydroformylation, an olefin (alkene) is reacted with a synthesis gas (a mixture of carbon monoxide and hydrogen) to give an aldehyde. Subsequent hydrogenation gives the actual oxo process alcohol. Oxo process alcohols serve as intermediates for the production of surfactants and/or plasticizers for plastic. Several million metric tons of oxo process alcohols are produced globally per year.

Since the hydrogenation of the aldehydes obtained by the hydroformylation is a necessary step in the preparation of oxo process alcohols, the present invention is concerned with a process of relevance on an industrial scale.

In industrial practice, oxo process aldehydes are generally hydrogenated in the liquid phase over heterogeneous fixed bed catalysts. On account of the large throughput volumes, the catalyst is of crucial importance for the process, since it determines the reaction rate and also the selectivity of the hydrogenation. The selection of a suitable catalyst is not trivial since the aldehydes to be hydrogenated never occur in pure form, but as a mixture of structurally isomeric aldehydes which is always accompanied by a large number of troublesome accompanying components which firstly bring about secondary reactions undesired in the hydrogenation and secondly damage the hydrogenation catalyst. Since the composition of the feed mixture comprising the aldehydes to be hydrogenated is determined by the upstream hydroformylation, the hydrogenation catalyst has to be exactly adjusted with respect to the particular hydroformylation.

For the hydrogenation of oxo process aldehydes, useful catalysts have been found to be those comprising a support material to which copper, chromium and nickel have been applied as active components.

A corresponding catalyst is disclosed in DE19842370A1. It comprises copper and nickel, each in a concentration range from 0.3% to 15% by weight and chromium in a proportion by weight of 0.05% by weight to 3.5% by weight. The support material used is porous silicon dioxide or aluminium oxide.

U.S. Pat. No. 4,677,234 describes a process for preparing ethylene glycol in the presence of a supported copper catalyst.

Although these catalysts have proven useful in the industrially practised hydrogenation of oxo process aldehydes, there is still a need for an alternative. The reason for this is the chromium content of these catalysts.

According to Annex XIV of the REACH directive, chromium-containing substances such as the catalysts described above must only be used in the European Union after authorization by the Commission. The granting of authorization is associated with great complexity and high costs; moreover, granting of authorization cannot be expected a priori. Moreover, the application procedure has to be repeated every five years.

The reason for these strict conditions is the undisputed carcinogenicity of the chromium used. This is of relevance firstly when the hydrogenation catalyst has to be disposed of following deactivation, and secondly when it is newly produced by impregnation with alkali metal chromates or alkali metal dichromates.

The chromium problem has been solved with the catalyst disclosed in EP3037400A1, which is virtually chromium-free. However, there is further need for improvement in this system, since nickel and the nickel compounds used in the production of the chromium-free catalyst are likewise carcinogenic.

In this respect, the problem addressed is that of specifying a catalyst system suitable for industrial hydrogenation of aldehydes, which is both free of chromium and free of nickel.

EP2488478B1 describes a two-stage hydrogenation of $C_{10}$ aldehydes, wherein a catalyst which is free of copper, chromium and nickel but does contain ruthenium is used in the second hydrogenation stage. Ru is comparatively costly, and for that reason this process is not always economically viable on the industrial scale. Furthermore, the process is not nickel-free either, since a nickel-containing catalyst has to be used in the first stage in order to achieve acceptable hydrogenation results.

WO95/32171A1 describes various hydrogenation catalysts comprising copper and silicon dioxide, either in the presence or absence of further elements including chromium. The specific chromium-free variants are notable for very high CuO contents (well above 20% by weight). The raw material costs for such copper-rich catalysts are quite high.

U.S. Pat. No. 3,677,969 describes an organometallic hydrogenation catalyst. A disadvantage of this system is that the production thereof is comparatively costly since it entails an additional sulphidation and it has to be heat-treated at very high temperatures (400° F. to 1000° F.). Moreover, an optional content of chromium and nickel is recommended.

In view of all the above, it has not been possible to date to find a chromium- and nickel-free catalyst suitable for the hydrogenation of hydroformylation mixtures on the industrial scale.

SUMMARY

In the light of this prior art, the problem addressed by the invention is that of developing a catalyst containing neither chromium nor nickel. other substances known to be carcinogenic are likewise to be absent. In addition, it is to enable the economically viable hydrogenation of aldehyde mixtures originating from industrial oxo processes on the industrial scale. For this purpose, the catalyst should not be reliant on costly precious metals such as Ru, Pd or Pt. The copper content of the catalyst should be at a minimum, in order to lower raw material costs. It is also in the interests of the production costs of the catalyst that the preparation thereof can be effected at low temperatures and the catalyst does not have to be sulphidated.

DETAILED DESCRIPTION

Figure 1:
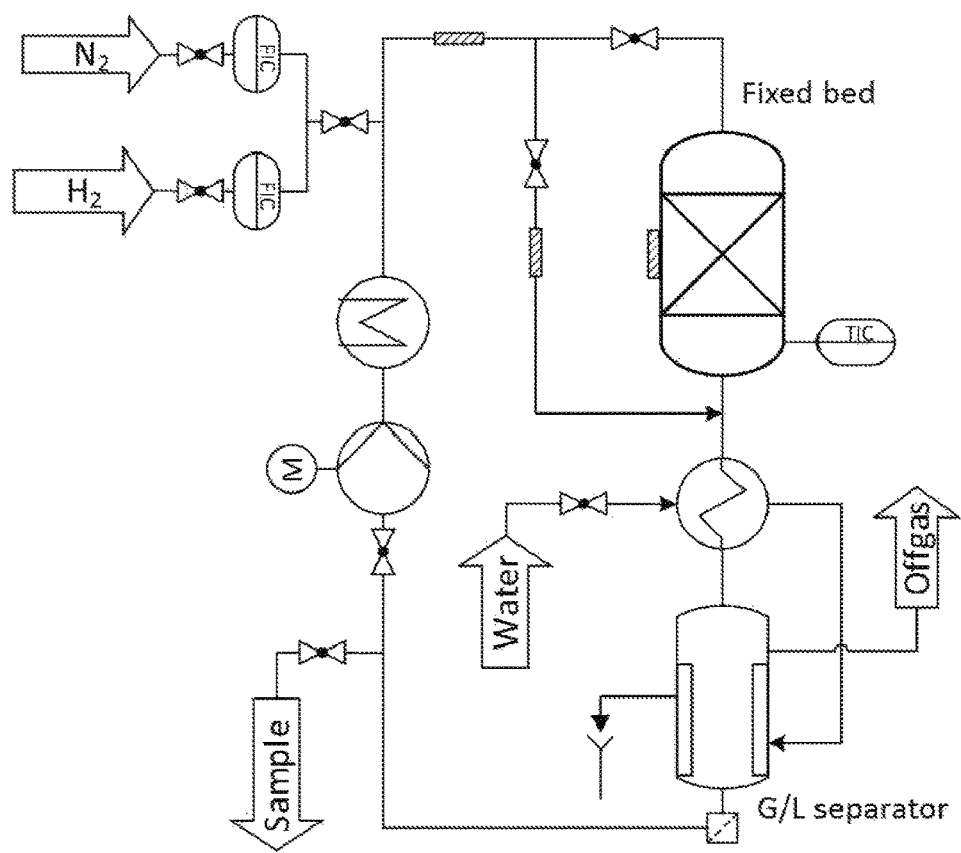
FIG. 1 representatively shows a plant flow diagram of the high-pressure batchwise hydrogenation apparatus used.

This problem was solved by omitting the chromium and nickel in the preparation of a conventional Cu/Ni/Cr system, such that a catalyst wherein only copper occurs as hydrogenation-active component on the support material thereof, and not chromium or nickel, is obtained. What is surprising here is that a functioning catalyst for the purpose intended still arises at all even though two of three hydrogenation-active metals are omitted. However, this requires as necessary conditions that support material used is silicon dioxide and that the content of Cu and $SiO_2$ in the active catalyst is set accurately within very tight limits. The reason why $SiO_2$ is particularly suitable as a support is probably because it contains very few Brønsted-acidic or Brønsted-basic sites, which accelerate by-product formation.

The invention therefore provides a process for preparing alcohols by hydrogenation of aldehydes, in which a feed mixture comprising at least one aldehyde and at least one accompanying component is contacted with a heterogeneous catalyst in the presence of hydrogen, giving a product mixture comprising at least the alcohol corresponding to the hydrogenated aldehyde, and at least one by-product, wherein the catalyst comprises a support material and copper applied thereto, wherein the support material is silicon dioxide and wherein the catalyst in activated form has the following composition that adds up to 100% by weight:
  silicon dioxide: from 86% by weight to 90% by weight;
  copper: from 10% by weight to 14% by weight;
  nickel: from 0 ppm by weight to 50 ppm by weight;
  chromium: from 0 ppm by weight to 50 ppm by weight;
  aluminium oxide: from 0 ppm by weight to 1000 ppm by weight;
  other substances: from 0 ppm by weight to 1% by weight.

"other substances" quote that in this connection are always understood to mean chemical elements or compounds thereof that are present in the catalyst but are explicitly mentioned in the enumeration. In the case of the above composition, "other substances" is thus a collective term for all components except $SiO_2$, Cu, Ni, Cr, $Al_2O_3$.

Examples of "other substances" may be carbonates, hydroxides, or simply intercalated water. Precious metals detectable in traces, such as Pt, Ru or Pd, are likewise covered by the term "other substances". For reasons of cost, according to the invention, the deliberate addition of precious metals in the preparation of the catalyst is dispensed with. However, it cannot be ruled out that traces of Pt, Ru or Pd can be detected in the catalyst prepared with the analytical options available nowadays. However, these would then be classified, just like residues of nickel and chromium, as unintentional contamination (by materials from the apparatuses or jewelry worn by personnel). Ideally, the content of "other substances" is zero.

A particularly suitable catalyst for the hydrogenation task has been found to be one which, in activated form, has the following composition that adds up to 100% by weight:
  silicon dioxide: from 87% by weight to 89% by weight;
  copper: from 11% by weight to 13% by weight;
  nickel: from 0 ppm by weight to 50 ppm by weight;
  chromium: from 0 ppm by weight to 50 ppm by weight;
  hydroxides: from 0 ppm by weight to 100 ppm by weight;
  ruthenium: from 0 ppm by weight to 50 ppm by weight;
  palladium: from 0 ppm by weight to 50 ppm by weight;
  platinum: from 0 ppm by weight to 50 ppm by weight;
  aluminium oxide: from 0 ppm by weight to 100 ppm by weight;
  water: from 0 ppm by weight to 100 ppm by weight;
  carbonates: from 0 ppm by weight to 100 ppm by weight;
  other substances: from 0 ppm by weight to 0.5% by weight.

The support material used in accordance with the invention is silicon dioxide. It is possible to use either fumed $SiO_2$ or precipitated silica as support material. Irrespective of the $SiO_2$ synthesis, the catalyst is always used in solid form with a greater or lesser crystalline component in the support material. The catalyst in the hydrogenation is thus a heterogeneous catalyst since it is not dissolved in the reaction mixture but present in another phase.

Preference is given to using a support material having a specific pore volume between 0.8 $cm^3/g$ and 1.2 $cm^3/g$, determined by the cyclohexane immersion method, and having a specific surface area (BET surface area) between 130 $m^2/g$ and 170 $m^2/g$, determined by ISO method 9277. A material of this kind is available as Aerolyst® 3041 from Evonik Resource Efficiency GmbH. It is based on fumed silicon dioxide.

In the interests of high process intensity, the hydrogenation is effected at a pressure between $15*10^5$ Pa and $25*10^5$ Pa and at a temperature between 140° C. and 180° C. Pressure and temperature should be chosen here such that feed mixture and product mixture are in a liquid phase.

Preferably, the hydrogen is supplied in a superstoichiometric amount in order to assure substantially full hydrogenation. However, the concentration of hydrogen should be set such that at least some of the hydrogen is dissolved in the liquid phase. Some of the hydrogen may also be in the gas phase and hence form bubbles in the reaction mixture. In that case, the reaction is effected in what is called "trickle bed" operation.

The catalyst system according to the invention was developed for hydrogenation of feed mixtures which originate from a hydroformylation and as such contain a plurality of aldehydes with the same number n of carbon atoms, and corresponding alcohols and high boilers, where n is a natural number between three and eighteen.

It has been optimized particularly for the hydrogenation of $C_9$ aldehyde mixtures having the following specification that adds up to 100% by weight:
- total fraction of the aldehydes having nine carbon atoms: 25% by weight to 75% by weight;
- total fraction of the alcohols having nine carbon atoms: 10% by weight to 55% by weight;
- total fraction of acetals: 0.5% by weight to 5.5% by weight;
- total fraction of further hydrocarbons: 0% by weight to 40% by weight;
- water: 0% by weight to 3% by weight.

Such a feed mixture is typically formed in the cobalt-catalysed hydroformylation of $C_8$ olefins.

It is particularly suitable for the hydrogenation of $C_9$ aldehyde mixtures having the following specification that adds up to 100% by weight:
- total fraction of the aldehydes having nine carbon atoms: 15% by weight to 65% by weight;
- total fraction of the alcohols having nine carbon atoms: 20% by weight to 65% by weight;
- total fraction of acetals: 0.5% by weight to 5.5% by weight;
- total fraction of further hydrocarbons: 0% by weight to 40% by weight;
- water: 0% by weight to 1% by weight.

Such a feed mixture is typically formed in the rhodium-catalysed hydroformylation of $C_8$ olefins.

The chemical and physical properties of a catalyst and hence the suitability thereof for the hydrogenation task is determined to a crucial degree by the preparation thereof.

Therefore, the preparation of the catalyst is an essential aspect of the invention. This is accomplished according to the claims essentially by the following steps:
a) providing a support material containing at least 99% by weight of silicon dioxide;
b) providing copper(II) hydroxide carbonate, ammonium hydrogencarbonate and/or ammonium carbonate, ammonia and water;
c) preparing a solution from copper(II) hydroxide carbonate, ammonium hydrogencarbonate and/or ammonium carbonate, ammonia and water, in such a way that the solution has a copper content between 10% by weight and 15% by weight, where the proportion of chromium in the solution is between 0 ppm by weight and 50 ppm by weight, and where the proportion of nickel in the solution is between 0 ppm by weight and 50 ppm by weight;
d) impregnating the support material with the solution;
e) drying the impregnated support material at temperatures between 50° C. and 150° C.;
f) calcining the dried, impregnated support material at temperatures between 300° C. and 600° C. to obtain a precursor;
g) activating the precursor by reduction with hydrogen to obtain the active catalyst.

More specifically, steps a) to f) relate to the preparation of the precursor, and step g) to the preparation of the actual catalyst from the precursor.

This distinction is important since the activation is often effected at a different location from the preparation of the precursor. The activation is usually effected in situ, i.e. at the site where hydrogenation is effected later, more specifically in the reactor. In such a case, the catalytically inactive precursor is installed into the hydrogenation reactor, then contacted with hydrogen for the purpose of reduction and hence activated. This has the advantage that copper oxides are not formed again by contact with atmospheric oxygen.

Alternatively, the catalyst is activated ex situ, i.e. reduced outside the hydrogenation reactor and supplied and installed in active form. However, this then has to be effected under a protective atmosphere, which is correspondingly costly and inconvenient.

Copper is required in the catalyst as hydrogenation-active metal. In the interests of catalyst costs, however, the copper content should be reduced to the necessary minimum. For this reason, it is advisable in the preparation of the solution in step c) to make up the solution in such a way that the copper content is between 10.5% by weight and 11.5% by weight. An optimal solution has been found to be one having a copper content of 11% by weight.

The impregnation of the support material with the solution can be effected in different ways. The solution is to penetrate into and very substantially fill the pores. The following procedure in the impregnation has been found to be useful: The support is introduced into a rotating drum. The solution is sprayed onto the support, and fills the pores. During the spraying phase, warm air can be passed through the rotating bed of the impregnated support. The warm air is generally air at a temperature in the region of the ambient temperature.

The impregnation in step d) and at least some of the drying of the impregnated support material in step e) is accordingly effected in accordance with the invention in a drum, in such a way that the support material is introduced into the drum for impregnation, that the drum is rotated, that the solution is sprayed into the drum, and that, during the drying phase, an air stream at a temperature between 50° C. and 100° C., preferably at a temperature of around 80° C., is passed through the drum. Steps d) and e) are thus undertaken with little manual labor in apparatus (the drum). This lowers the production costs.

In a further embodiment of the present invention, it is likewise possible to remove the impregnated support material from the drum before drying is complete and to dry it to completion in a dryer in an air stream within the temperature range from 100° C. to 150° C. The transfer from the drum to the dryer is an additional process step, but can lead to a low water content.

The handling of the catalyst in its preparation and in the installation into the reactor is significantly facilitated when the support material provided comprises cylindrical extrudates having a diameter between 1 mm and 2 mm. The catalyst can then be handled like a bulk material. In the liquid phase hydrogenation, the cylindrical extrudates are favorable in terms of flow dynamics. Aerolyst® 3014 from Evonik is available in this preferred presentation form. As an alternative form of catalyst, it is also possible to use spheres in the diameter range between 1 mm and 2 mm.

Prior to activation, the precursor preferably has the following composition that adds up to 100% by weight:
- silicon dioxide: from 84% by weight to 86% by weight;
- copper oxide: from 14% by weight to 16% by weight;
- nickel: from 0 ppm by weight to 50 ppm by weight;
- chromium: from 0 ppm by weight to 50 ppm by weight;
- aluminium oxide: from 0 ppm by weight to 1000 ppm by weight;
- other substances: from 0 ppm by weight to 1% by weight.

It is important that the copper in this precursor is still in oxidic form. Because of the bound oxygen, there is a difference in the total weight of the precursor from the active catalyst, and for that reason there is also a difference in the relative stated amounts.

In the activation, the CuO is reduced with $H_2$ to Cu. The water formed at the same time is drawn off. Because the copper catalyst is now metallic, the catalyst is now hydrogenation-active. On conclusion of the activation, the oxygen has been removed, and so the active catalyst has the composition of the invention. Preferably, the catalyst is reduced in situ with liquid hydrogen. Alternatively, the catalyst can be efficiently activated in the gas phase.

The invention likewise provides for the use of the catalysts prepared in this manner in processes for preparing alcohols by hydrogenation of aldehydes according to the present invention.

The described preparation of the precursor, the activation thereof and the use of the active catalyst in the hydrogenation of aldehydes together solve the stated problem.

The invention therefore also provides a combined process for preparing a precursor, activating the precursor to give an active catalyst and using the catalyst for hydrogenation of aldehydes. The process according to the invention for hydrogenation of aldehydes accordingly comprises the following steps:
a) providing a support material containing at least 99% by weight of silicon dioxide;
b) providing copper(II) hydroxide carbonate, ammonium hydrogencarbonate and/or ammonium carbonate, ammonia and water;
c) preparing a solution comprising copper(II) hydroxide carbonate, ammonium hydrogencarbonate and/or ammonium carbonate, ammonia and water, in such a way that the solution has a copper content between 10% by weight and 15% by weight, where the proportion of chromium in the solution is between 0 ppm by weight and 50 ppm by weight, and where the proportion of nickel in the solution is between 0 ppm by weight and 50 ppm by weight;
d) impregnating the support material with the solution;
e) drying the impregnated support material at temperatures between 50° C. and 150° C.;
f) calcining the dried impregnated support material at temperatures between 300° C. and 600° C. to obtain a precursor especially having the following composition that adds up to 100% by weight:
silicon dioxide: from 84% by weight to 86% by weight;
copper oxide: from 14% by weight to 16% by weight;
nickel: from 0 ppm by weight to 50 ppm by weight;
chromium: from 0 ppm by weight to 50 ppm by weight;
aluminium oxide: from 0 ppm by weight to 1000 ppm by weight;
other substances: from 0 ppm by weight to 1% by weight.
g) transferring the precursor to a reactor;
h) activating the precursor in the reactor by reduction with hydrogen to obtain the active catalyst especially having the following composition that adds up to 100% by weight:
silicon dioxide: from 86% by weight to 90% by weight;
copper: from 10% by weight to 14% by weight;
nickel: from 0 ppm by weight to 50 ppm by weight;
chromium: from 0 ppm by weight to 50 ppm by weight;
aluminium oxide: from 0 ppm by weight to 1000 ppm by weight;
other substances: from 0 ppm by weight to 1% by weight.
i) contacting the active catalyst in the reactor with a feed mixture comprising at least one aldehyde and at least one accompanying component in the presence of hydrogen, especially giving a product mixture comprising at least the alcohol corresponding to the hydrogenated aldehyde and at least one by-product,
wherein the impregnation and at least some of the drying is effected in a drum, in such a way that the support material is introduced into the drum for impregnation, that the drum is rotated, that the solution is sprayed into the drum, and that, during the drying phase, an air stream at a temperature between 50° C. and 100° C. is passed through the drum.

The invention will now be elucidated in detail with reference to examples. For this purpose, the figures show:

FIG. 1: Plant flow diagram of the high-pressure batchwise hydrogenation apparatus used FIG. 2: Conversion and selectivity plot in the batchwise hydrogenation of a C9 aldehyde mixture with a chromium- and nickel-containing catalyst FIG. 3: Conversion and selectivity plot in the batchwise hydrogenation of a C9 aldehyde mixture with a chromium- and nickel-free catalyst ("catalyst A")

Figure 4:
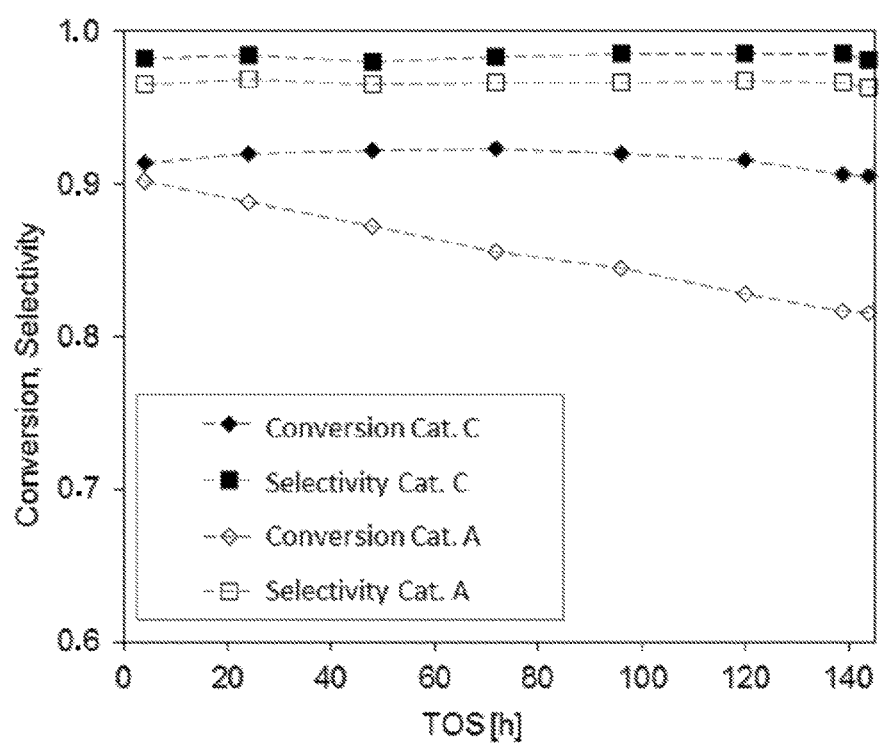
FIG. 4 representatively shows a Conversion and selectivity plot in the continuous hydrogenation of a C9 aldehyde mixture with a chromium- and nickel-containing catalyst A and a chromium- and nickel-free catalyst C.

FIG. 4: Conversion and selectivity plot in the continuous hydrogenation of a C9 aldehyde mixture with a chromium- and nickel-containing catalyst A and a chromium- and nickel-free catalyst C.

Example 0: Preparation of a Precursor of a Chromium-Free and Nickel-Free Cu/SiO$_2$ Catalyst An SiO$_2$ support is impregnated with an aqueous copper tetraammine carbonate solution (prepared in accordance with the invention from copper (II) hydroxide carbonate, ammonium hydrogencarbonate and/or ammonium carbonate, ammonia and water) at ambient temperature. This is followed by drying in an air stream at moderate temperatures. Finally, calcination is effected in air at 450° C.

The support material used is Aerolyst® 3041 from Evonik. The typical properties thereof are an SiO$_2$ content greater than 99%, cylindrical extrudates having diameters of around 1.7 mm, pore volumes of about 1 cm$^3$/g and BET surface areas of about 150 m$^2$/g.

Copper hydroxide carbonate, concentrated ammonia solution, ammonium hydrogencarbonate and/or ammonium carbonate and water are used to prepare a copper tetraammine solution containing about 13% by weight of copper. The solution was then diluted once again with water to about 11% by weight of copper.

For the purpose of impregnation, the dilute copper tetraammine carbonate solution was then sprayed onto the support material. In the impregnation, the support rotates in a drum. During the spraying operation, a certain amount of air was passed through the fixed bed. The amount of spray solution applied is such that, after the impregnation, virtually all pores have been filled with liquid and the copper salt solution is distributed over the entire grain.

The drying was effected in the same drum. For this purpose, the air stream which is passed through the drum and fixed bed was heated to temperatures of about 75° C. In this specific case, the catalyst, prior to the calcination, was subjected to further drying in a further reactor at 120° C. in an air stream.

The calcination, in which the copper salt is essentially converted to copper oxide, was effected in an oven through which a continuous air stream flowed; the GHSV (gas hourly space velocity) was 2000 h$^{-1}$; the catalyst was calcined at 450° C. for 10 h in air.

In principle, the catalyst can be prepared by any impregnation processes in which the pores of the support are filled with the solution; examples of these also include vacuum impregnation or the immersion of the support with excess solution.

Drying can also be effected in other customary industrial units (shaft dryers, chamber ovens, belt dryers, drum dryers, vacuum dryers); typical drying temperatures are between 50° C. and 150° C.

It is also possible to use different units in the calcination: shaft furnaces, chamber furnaces, rotary furnaces, etc. The temperature of 450° C. is certainly not extremely crucial either; somewhat lower temperatures or else higher temperatures are conceivable here too.

The precursor prepared in this way contained 15% by weight of CuO and about 85% by weight of $SiO_2$.

For the purpose of activation to give the catalyst, the precursor is contacted with a gaseous hydrogen stream at $10*10^5$ Pa at 60 l/h (STP). The temperature was increased here in 30 K steps every hour from 60° C. to 180° C. and kept constant for 12 h.

Example 1 (Noninventive): Hydrogenation of $C_9$ Aldehydes from a Co-Catalysed Hydroformylation at 180° C. with a Chromium- and Nickel-Containing Catalyst The catalyst A used is a chromium-containing catalyst as also used for the experiments described in DE19842370A1.

For the performance of the batchwise hydrogenation experiments, a 1 l high-pressure stainless steel reactor stirred by means of external circuit was used. The reactor has an insert for catalyst filling having a diameter of 4 cm and a length of 30 cm. A simplified flow diagram of the plant is shown in FIG. 1.

The reactor and the conduits were heated by means of wound heating tapes, and the temperature was controlled and regulated by means of PT100 thermocouples. The liquid phase was circulated by means of a Gather DS2X30 gear pump with circulation rates of 45 l/h. The temperature of the liquid phase was controlled with the aid of a LAUDA LTH350s thermostat. The heat carrier used was MARLOTHERM SH. For the separation of the phases, a stainless steel vessel (capacity 2 l) was installed and cooled continuously with water. The phase separator served simultaneously as reservoir for the liquid reactant. The hydrogen and nitrogen supply was regulated by means of Bronkhorst F231M or F231C mass flow meters. Prior to the performance of batch experiments, 90 ml of catalyst A (dry) were introduced into the catalyst basket and installed in the reactor. The fresh hydrogenation catalysts were reduced in a hydrogen stream at $10*10^5$ Pa at 60 l (STP)/h. The temperature was increased here in 30 K steps every hour from 60° C. to 180° C. and kept constant for 12 h. The phase separator was charged with 1 l of reactant and the liquid phase was heated in circulation through the reactor bypass. On attainment of the desired reaction temperature, a bypass sample was taken and the reaction was started by opening the reactor tap. During the reaction, samples were taken at defined times and analysed via offline GC (7890B GC; from Agilent Technologies).

Figure 2:
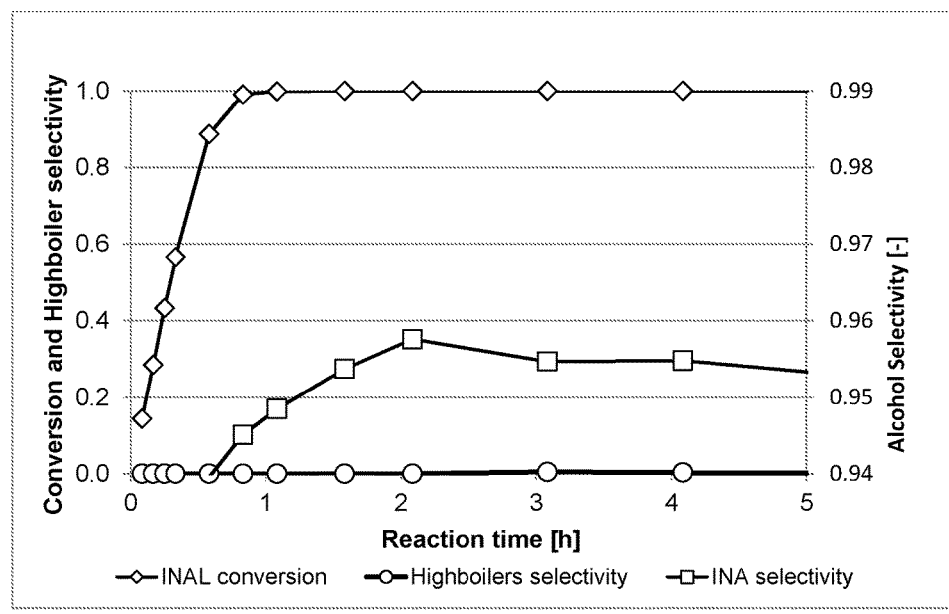
FIG. 2 representatively shows a conversion and selectivity plot in the batchwise hydrogenation of a C9 aldehyde mixture with a chromium- and nickel-containing catalyst.
Figure 3:
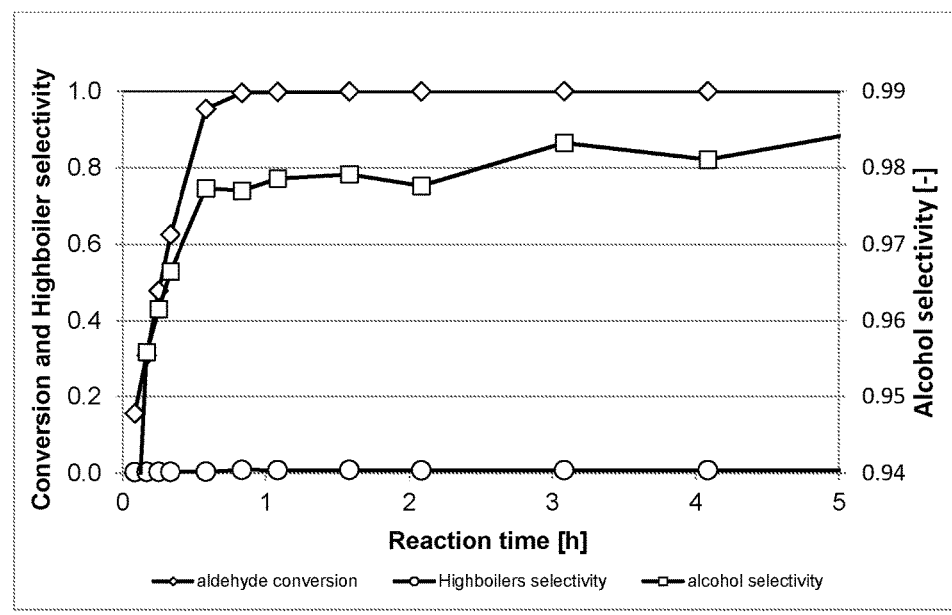
FIG. 3 representatively shows a conversion and selectivity plot in the batchwise hydrogenation of a C9 aldehyde mixture with a chromium- and nickel-free catalyst ("catalyst A")

The conversions and selectivities achieved in this experiment are shown in the form of a graph in FIG. 2.

Example 2 (Inventive): Hydrogenation of $C_9$ Aldehydes from a Co-Catalysed Hydroformylation at 180° C. with a Chromium- and Nickel-Free Catalyst The batchwise hydrogenation with the chromium- and nickel-free catalyst from Example 0 ("catalyst C") is conducted as described in Example 1. Catalyst A is replaced here by catalyst C. The conversion and selectivity plot shows that a much higher alcohol selectivity can be achieved with catalyst C.

Example 3: Long-Term Comparison of a Chromium- and Nickel-Containing Catalyst with A Chromium- and Nickel-Free Catalyst The parallelized evaluation of alternative hydrogenation catalysts was effected in a continuously operated 16-channel system for testing of heterogeneous catalyst systems. The system has a central reactor block with 16 separate stainless steel reactors having a length of 96 cm and an internal diameter of 5 mm. The reactor block is heated electrically and permits isothermal operation of the reactors with an accuracy of ±1° C. A system of capillary restrictors is used to distribute and meter in the liquid and gaseous reactants; the pressure retention of the reactors is based on backpressure membrane modules from Equilibar. For the evaluation of the hydrogenation catalysts, after estimation of the catalyst activity from the batchwise experiments described in Examples 1 and 2, 0.2 g to 0.6 g of catalyst (in dry form) was used in the form of sieve fraction (0.2 mm to 0.4 mm) and diluted with crushed quartz (0.3 mm to 0.5 mm). The catalysts used were always diluted in such a way that a constant length of the catalytically active bed of 10 cm was produced. The liquid phase hydrogenation is conducted in trickle bed operation; hydrogen has to be fed in in gaseous form here. The hydrogen is then partly dissolved in the liquid phase and partly in the form of bubbles in the gas phase. In addition, there is an offgas flow in order to avoid the accumulation of gaseous by-products. The testing was therefore effected at a temperature of 180° C. and a hydrogen pressure of $25*10^5$ Pa at an LHSV (liquid hourly space velocity) of 6 $h^{-1}$ and a GHSV (gas hourly space velocity of the gaseous hydrogen) of 2000 $h^{-1}$. All measurements were effected as a double determination. The product samples were analysed by offline GC (7890B GC; from Agilent Technologies), analogously to the hydrogenation experiments according to Example 1 and Example 2.

As shown by the conversion and selectivity plot of this comparison shown in FIG. 4, it is possible with the chromium- and nickel-free catalyst C inventive to achieve constantly high alcohol selectivity above that of the chromium- and nickel-containing comparative catalyst A over the entire duration of the experiment. At the same time, catalyst C is notable for a much smaller decrease in the degree of conversion compared to catalyst A.

CONCLUSION

The comparison of the examples shows that it is possible using the Cr- and Ni-free Cu catalyst according to the invention to hydrogenate $C_5$, $C_9$, $C_{13}$ and $C_{17}$ aldehyde mixtures obtained from industrial hydroformylation, at the same time obtaining product mixtures containing a high proportion of the corresponding aldehydes, while the proportion of the unwanted by-products is small.

Viewed over a prolonged period, the aldehyde yields from the chromium- and nickel-free experiments are not significantly poorer than the comparative experiments with conventional Ni/Cu/Cr systems.

In the preparation of the chromium- and nickel-free catalyst, it is possible to avoid handling carcinogenic substances. The use of precious metals is unnecessary. No additional working steps in the preparation of the catalyst, for example a sulphidation, were required. In the preparation, no high temperatures were necessary. The hydrogenation results are entirely satisfactory. The catalyst seems to be economically usable in industry.

The invention claimed is:

1. A process for preparing alcohols by hydrogenation of aldehydes, in which a feed mixture comprises the step of
    a) contacting an aldehyde and an accompanying component is contacted with a heterogeneous catalyst in the presence of hydrogen, giving a product mixture comprising the alcohol corresponding to the hydrogenated aldehyde, and a by-product,
    wherein the heterogeneous catalyst comprises a support material and copper applied thereto,
    wherein the support material is silicon dioxide;
    and the catalyst in activated form has the following composition that adds up to 100% by weight:
    silicon dioxide: from 86% by weight to 90% by weight;
    copper: from 10% by weight to 14% by weight;
    nickel: from 0 ppm by weight to 50 ppm by weight;
    chromium: from 0 ppm by weight to 50 ppm by weight;
    aluminium oxide: from 0 ppm by weight to 1000 ppm by weight;
    other substances: from 0 ppm by weight to 1% by weight
    wherein the support material makes up from 86% to 90% by of the composition and the remaining components set forth above make up from 10% to 14% by weight of the composition and wherein the yield of the alcohol is from 95% to 99%.

2. The process according to claim 1, wherein the heterogeneous catalyst in activated form has the following composition adding up to 100% by weight:
    silicon dioxide: from 87% by weight to 89% by weight;
    copper: from 11% by weight to 13% by weight;
    nickel: from 0 ppm by weight to 50 ppm by weight;
    chromium: from 0 ppm by weight to 50 ppm by weight;
    ruthenium: from 0 ppm by weight to 50 ppm by weight;
    palladium: from 0 ppm by weight to 50 ppm by weight;
    platinum: from 0 ppm by weight to 50 ppm by weight;
    aluminium oxide: from 0 ppm by weight to 100 ppm by weight;
    water: from 0 ppm by weight to 100 ppm by weight;
    carbonates: from 0 ppm by weight to 100 ppm by weight;
    hydroxides: from 0 ppm by weight to 100 ppm by weight;
    other substances: from 0 ppm by weight to 0.5% by weight
    wherein the support material makes up from 87% to 89% by of the composition and the remaining components set forth above make up from 11% to 13% by weight of the composition.

3. The process according to claim 1, wherein the specific pore volume of the support material is between 0.8 cm$^3$/g and 1.2 cm$^3$/g, determined by the cyclohexane immersion method, and in that the specific surface area of the support material (BET surface area) is between 130 m$^2$/g and 170 m$^2$/g, determined by ISO method 9277.

4. The process according to claim 1, wherein it is conducted at a pressure between $15*10^5$ Pa and $25*10^5$ Pa and at a temperature between 140° C. and 180° C., the pressure and temperature being chosen such that feed mixture and product mixture are in a liquid phase.

5. The process according to claim 4, wherein the hydrogen is present in a superstoichiometric amount, the concentration of the hydrogen being chosen such that at least some of the hydrogen is dissolved in the liquid phase.

6. The process according to claim 1, wherein the feed mixture originates from a hydroformylation and as such comprises a plurality of aldehydes with the same number n of carbon atoms, and corresponding alcohols and high boilers, where n is a natural number between three and eighteen.

7. The process according to claim 6, wherein the feed mixture has the following composition that adds up to 100% by weight:
    total fraction of the aldehydes having nine carbon atoms: 25% by weight to 75% by weight;
    total fraction of the alcohols having nine carbon atoms: 10% by weight to 55% by weight;
    total fraction of acetals: 0.5% by weight to 5.5% by weight;
    total fraction of further hydrocarbons: 0% by weight to 40% by weight;
    water: 0% by weight to 3% by weight.

8. The process according to claim 6, wherein the feed mixture has the following composition that adds up to 100% by weight:
    total fraction of the aldehydes having nine carbon atoms: 15% by weight to 65% by weight;
    total fraction of the alcohols having nine carbon atoms: 20% by weight to 65% by weight;
    total fraction of acetals: 0.5% by weight to 5.5% by weight;
    total fraction of further hydrocarbons: 0% by weight to 40% by weight;
    water: 0% by weight to 1% by weight.

9. A process for preparing a catalyst, comprising the following steps:
    a) providing a support material containing at least 99% by weight of silicon dioxide;
    b) providing copper(II) hydroxide carbonate, ammonium hydrogencarbonate and/or ammonium carbonate, ammonia and water;
    c) preparing a solution from copper(II) hydroxide carbonate, ammonium hydrogencarbonate and/or ammonium carbonate, ammonia and water, in such a way that the copper content of the solution is between 10% by weight and 15% by weight, where the proportion of chromium in the solution is between 0 ppm by weight and 50 ppm by weight, and where the proportion of nickel in the solution is between 0 ppm by weight and 50 ppm by weight wherein the support material makes up from 86% to 90% by of the composition and the remaining components set forth above make up from 10% to 14% by weight of the composition;
    d) impregnating the support material with the solution;
    e) drying the impregnated support material at temperatures between 50° C. and 150° C.;
    f) calcining the dried, impregnated support material at temperatures between 300° C. and 600° C. to obtain a precursor;
    g) activating the precursor by reduction with hydrogen to obtain the active catalyst,
    wherein the impregnation and at least part of the drying is effected in a drum, in such a way that the support material is introduced into the drum for impregnation, that the drum is rotated, that the solution is sprayed into the drum, and that, during the drying phase, an air stream at a temperature between 50° C. and 100° C. is passed through the drum.

10. The process according to claim 9, wherein the copper content of the solution is between 10.5% by weight and 11.5% by weight.

11. Process according to claim 9, wherein the support material provided comprises cylindrical extrudates having a diameter between 1 mm and 2 mm.

12. Process according to claim 9, wherein the precursor has the following composition that adds up to 100% by weight:
    silicon dioxide: from 84% by weight to 86% by weight;
    copper oxide: from 14% by weight to 16% by weight;
    nickel: from 0 ppm by weight to 50 ppm by weight;
    chromium: from 0 ppm by weight to 50 ppm by weight;
    aluminium oxide: from 0 ppm by weight to 1000 ppm by weight;
    other substances: from 0 ppm by weight to 1% by weight
    wherein the support material makes up from 84% to 86% by of the composition and the remaining components set forth above make up from 14% to 16% by weight of the composition.

13. A process for hydrogenation of aldehydes, comprising the following steps:
    a) providing a support material containing at least 99% by weight of silicon dioxide;
    b) providing copper(II) hydroxide carbonate, ammonium hydrogencarbonate and/or ammonium carbonate, ammonia and water;
    c) preparing a solution from copper(II) hydroxide carbonate, ammonium hydrogencarbonate and/or ammonium carbonate, ammonia and water, in such a way that the solution has a copper content between 10% by weight and 15% by weight, where the proportion of chromium in the solution is between 0 ppm by weight and 50 ppm by weight, and where the proportion of nickel in the solution is between 0 ppm by weight and 50 ppm by weight wherein the support material makes up from 86% to 90% by of the composition and the remaining components set forth above make up from 10% to 14% by weight of the composition;
    d) impregnating the support material with the solution;
    e) drying the impregnated support material at temperatures between 50° C. and 150° C.;
    f) calcining the dried impregnated support material at temperatures between 300° C. and 600° C. to obtain a precursor,
    g) transferring the precursor to a reactor;
    h) activating the precursor in the reactor by reduction with hydrogen to obtain the active catalyst,
    i) contacting the active catalyst in the reactor with a feed mixture comprising at least one aldehyde and at least one accompanying component in the presence of hydrogen
    wherein the impregnation and at least part of the drying is effected in a drum, in such a way that the support material is introduced into the drum for impregnation, that the drum is rotated, that the solution is sprayed into the drum, and that, during the drying phase, an air stream at a temperature between 50° C. and 100° C. is passed through the drum.

14. The process according to claim 2, wherein the specific pore volume of the support material is between 0.8 $cm^3/g$ and 1.2 $cm^3/g$, determined by the cyclohexane immersion method, and in that the specific surface area of the support material (BET surface area) is between 130 $m^2/g$ and 170 $m^2/g$, determined by ISO method 9277.

15. The process according to claim 2, wherein it is conducted at a pressure between $15*10^5$ Pa and $25*10^5$ Pa and at a temperature between 140° C. and 180° C., the pressure and temperature being chosen such that feed mixture and product mixture are in a liquid phase.

16. The process according to claim 3, wherein it is conducted at a pressure between $15*10^5$ Pa and $25*10^5$ Pa and at a temperature between 140° C. and 180° C., the pressure and temperature being chosen such that feed mixture and product mixture are in a liquid phase.

17. The process according to claim 2, wherein the feed mixture originates from a hydroformylation and as such comprises a plurality of aldehydes with the same number n of carbon atoms, and corresponding alcohols and high boilers, where n is a natural number between three and eighteen.

18. The process according to claim 17, wherein the feed mixture has the following composition that adds up to 100% by weight:
    total fraction of the aldehydes having nine carbon atoms: 25% by weight to 75% by weight;
    total fraction of the alcohols having nine carbon atoms: 10% by weight to 55% by weight;
    total fraction of acetals: 0.5% by weight to 5.5% by weight;
    total fraction of further hydrocarbons: 0% by weight to 40% by weight;
    water: 0% by weight to 3% by weight.

19. The process according to claim 10, wherein the support material provided comprises cylindrical extrudates having a diameter between 1 mm and 2 mm.

20. The process according to claim 10, wherein the precursor has the following composition that adds up to 100% by weight:
    silicon dioxide: from 84% by weight to 86% by weight;
    copper oxide: from 14% by weight to 16% by weight;
    nickel: from 0 ppm by weight to 50 ppm by weight;
    chromium: from 0 ppm by weight to 50 ppm by weight;
    aluminium oxide: from 0 ppm by weight to 1000 ppm by weight;
    other substances: from 0 ppm by weight to 1% by weight
    wherein the support material makes up from 84% to 86% by of the composition and the remaining components set forth above make up from 14% to 16% by weight of the composition.

* * * * *

UNITED STATES PATENT AND TRADEMARK OFFICE
CERTIFICATE OF CORRECTION

| | |
|---|---|
| PATENT NO. | : 10,245,578 B2 |
| APPLICATION NO. | : 15/790800 |
| DATED | : April 2, 2019 |
| INVENTOR(S) | : Florian Klasovsky et al. |

It is certified that error appears in the above-identified patent and that said Letters Patent is hereby corrected as shown below:

In the Claims

Column 11,
Lines 8-9, Claim 1: "accompanying component is contacted with" should read -- accompanying component contacted with --.

Signed and Sealed this
Seventh Day of May, 2019

Andrei Iancu
*Director of the United States Patent and Trademark Office*